United States Patent
Zukowski (10) Patent No.: US 9,173,753 B1
(45) Date of Patent: Nov. 3, 2015

(54) SYSTEM AND METHOD FOR FORMING AN ENDOLUMINAL DEVICE

(71) Applicant: W. L. Gore & Associates, Inc., Newark, DE (US)

(72) Inventor: Stanislaw L. Zukowski, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 382 days.

(21) Appl. No.: 13/888,240

(22) Filed: May 6, 2013

Related U.S. Application Data (60) Provisional application No. 61/646,142, filed on May 11, 2012.

(51) Int. Cl.
*A61F 2/88* (2006.01)
*B21F 3/04* (2006.01)

(52) U.S. Cl.
CPC .... *A61F 2/88* (2013.01); *B21F 3/04* (2013.01)

(58) Field of Classification Search
CPC ............... B21F 3/04; B21F 3/12; A61F 2/86; A61F 2/88; A61F 2/89
USPC .......................................... 72/142, 144, 145
See application file for complete search history.

(56) References Cited

U.S. PATENT DOCUMENTS

| | | |
|---|---|---|
| 2,896,689 A | 7/1959 | Arms |
| 3,736,784 A | 6/1973 | Felker |
| 3,838,617 A | 10/1974 | Felker |
| 4,012,272 A | 3/1977 | Tiner |
| 4,357,967 A | 11/1982 | Feldshtein et al. |
| 5,084,606 A | 1/1992 | Bailey et al. |
| 5,554,181 A * | 9/1996 | Das .............................. 623/1.12 |
| 6,279,368 B1 | 8/2001 | Escano et al. |
| 6,416,541 B2 | 7/2002 | Denardo |
| 6,432,134 B1 | 8/2002 | Anson et al. |
| 6,496,154 B2 | 12/2002 | Gyenes |
| 6,585,759 B1 | 7/2003 | Baum et al. |
| 6,619,024 B1 | 9/2003 | Strobel et al. |
| 2004/0186549 A1 | 9/2004 | Jayaraman |
| 2007/0043428 A1 | 2/2007 | Jennings et al. |
| 2007/0043430 A1 | 2/2007 | Stinson |
| 2008/0021535 A1 | 1/2008 | Leopold et al. |
| 2008/0195139 A1 | 8/2008 | Donald et al. |
| 2008/0196382 A1 | 8/2008 | Rozenvasser |
| 2009/0188092 A1 | 7/2009 | Teresiak |
| 2010/0179644 A1 | 7/2010 | Jennings et al. |

FOREIGN PATENT DOCUMENTS

| | | |
|---|---|---|
| CA | 816460 | 7/1969 |
| GB | 1092405 | 11/1967 |
| RU | 2257977 | 8/2005 |
| RU | 2264882 | 11/2005 |

* cited by examiner

*Primary Examiner* — Debra Sullivan
(74) *Attorney, Agent, or Firm* — Gilbert R. Gabo; David J. Johns (57) ABSTRACT

The present disclosure describes a system and method for forming a stent or stent-graft for use in the vasculature of a human patient. The system comprises a mandrel and a collar configured to slide and rotate in relation to the mandrel. The mandrel includes at least one groove that corresponds to the desired shape of a stent or stent-graft. The stent or stent-graft is formed by sliding and rotating the collar along the surface of the mandrel, which forces a wire to conform to the shape of the groove.

20 Claims, 12 Drawing Sheets

SYSTEM AND METHOD FOR FORMING AN ENDOLUMINAL DEVICE

CROSS REFERENCE TO RELATED APPLICATIONS

This application claims priority to U.S. Provisional Application No. 61/646,142, Filed May 11, 2012. The disclosure of the prior application is considered part of and is incorporated by reference in the disclosure of this application.

BACKGROUND

Field

Endoluminal devices such as stents, grafts, filters, valves, anchors, occluders, and other implantable devices are frequently used to treat the vasculature of human patients. Such devices often include a frame comprising a stent that can be used alone or in connection with other materials such as graft or filtering materials. The design and/or manufacture of these devices can be labor and time intensive, as they often require a technician to manually wind a wire into the shape of the desired stent. Therefore, it is desirable to provide a system and method for forming stents that is less time and labor intensive than the current stent formation systems and methods.

BRIEF DESCRIPTION OF THE DRAWINGS

The accompanying drawings are included to provide a further understanding of the disclosure and are incorporated in and constitute a part of this specification, illustrate embodiments of the disclosure, and together with the description, serve to explain the principles of the disclosure, wherein.

DETAILED DESCRIPTION OF THE ILLUSTRATED EMBODIMENTS

Persons skilled in the art will readily appreciate that various aspects of the present disclosure can be realized by any number of methods and systems configured to perform the intended functions. Stated differently, other methods and systems can be incorporated herein to perform the intended functions. It should also be noted that the accompanying drawing figures referred to herein are not all drawn to scale, but can be exaggerated to illustrate various aspects of the present disclosure, and in that regard, the drawing figures should not be construed as limiting. Finally, although the present disclosure can be described in connection with various principles and beliefs, the present disclosure should not be bound by theory.

Endoluminal devices such as stents, grafts, filters, valves, anchors, occluders, and other implantable devices are frequently used to treat the vasculature of human patients. These treatments or procedures are commonly referred to as intraluminal or endovascular procedures. Such endoluminal devices, including stents and stent-grafts, can be generally tube like structures that define a lumen and that can be inserted into the vasculature to open and/or maintain the vasculature in order to prevent or address localized flow constriction, weakening of the vasculature wall, aneurysms, etc.

Figure 1:
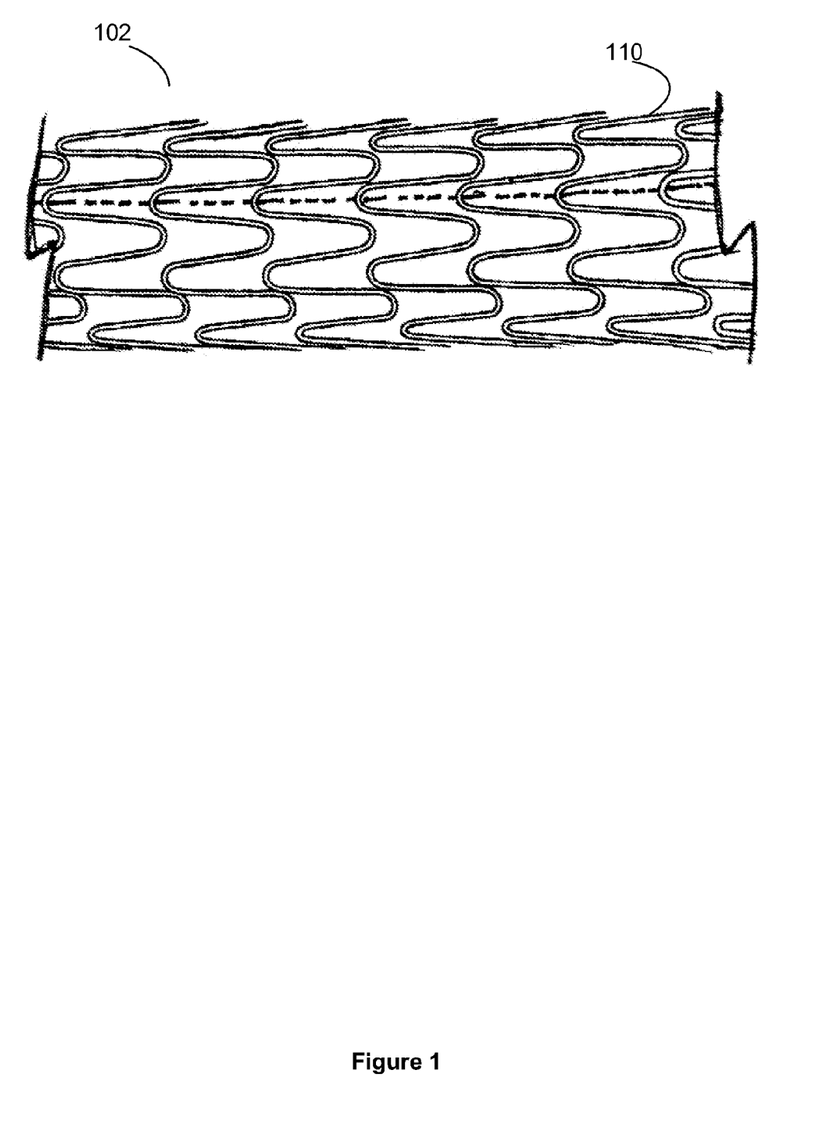
FIG. 1 illustrates a perspective view of an endoluminal device.

For example, with reference to FIG. 1, a stent 102 in accordance with the present disclosure is illustrated. For example, stent 102 can have various configurations such as, for example, wound wires (or ribbons). Stent components can be formed from metallic, polymeric or natural materials and can comprise conventional medical grade materials such as nylon, polyacrylamide, polycarbonate, polyethylene, polyformaldehyde, polymethylmethacrylate, polypropylene, polytetrafluoroethylene, polytrifluorochlorethylene, polyvinylchloride, polyurethane, elastomeric organosilicon polymers; metals such as stainless steels, cobalt-chromium alloys and Nitinol and biologically derived materials such as bovine arteries/veins, pericardium and collagen. Stent 102 can also comprise bioresorbable materials such as poly(amino acids), poly(anhydrides), poly(caprolactones), poly(lactic/glycolic acid) polymers, poly(hydroxybutyrates) and poly(orthoesters).

In some embodiments, stent 102 is comprised of a shape-memory material, such as, but not limited to, Nitinol. In other embodiments, however, stent 102 can be comprised of other materials, self-expandable or otherwise expandable (e.g., with a balloon or spring mechanism), such as various metals (e.g., stainless steel), alloys, and polymers. Any stent 102 configuration that can be delivered by a catheter is in accordance with the present disclosure.

In various embodiments, stent 102 comprises a single wire 110 with a generally sinusoidal configuration. For example, with momentary reference to FIG. 3B, stent 102 can comprise a generally sinusoidal pattern 320 having a plurality of peaks 324 and a plurality of valleys 326. Such a pattern can further comprise an amplitude and a period. In the present disclosure, for example, "amplitude" refers to amplitude 328, namely the height difference between the peaks 324 and valleys 326 of stent 102. In the present disclosure, "period" refers period 332, namely the circumferential distance between peak 324 and an adjacent peak 324 of stent 102. However, any pattern that provides sufficient resilience and flexibility to stent 102 is within the scope of the present disclosure.

In various embodiments, the stent 102 has dimensions appropriate for the desired vascular treatment and with sufficient strength to provide structural support for the flexible wall of the endoluminal device and/or the vasculature.

In various embodiments, a stent 102 can further comprise a therapeutic coating. In these embodiments, the interior or exterior of the stent 102 can be coated with, for example, a CD34 antigen. Additionally, any number of drugs or therapeutic agents can be used to coat the graft member, including, for example heparin, sirolimus, paclitaxel, everolimus, ABT-578, mycophenolic acid, tacrolimus, estradiol, oxygen free radical scavenger, biolimus A9, anti-CD34 antibodies, PDGF receptor blockers, MMP-1 receptor blockers, VEGF, G-CSF, HMG-CoA reductase inhibitors, stimulators of iNOS and eNOS, ACE inhibitors, ARBs, doxycycline, and thalidomide, among others.

Figure 2:
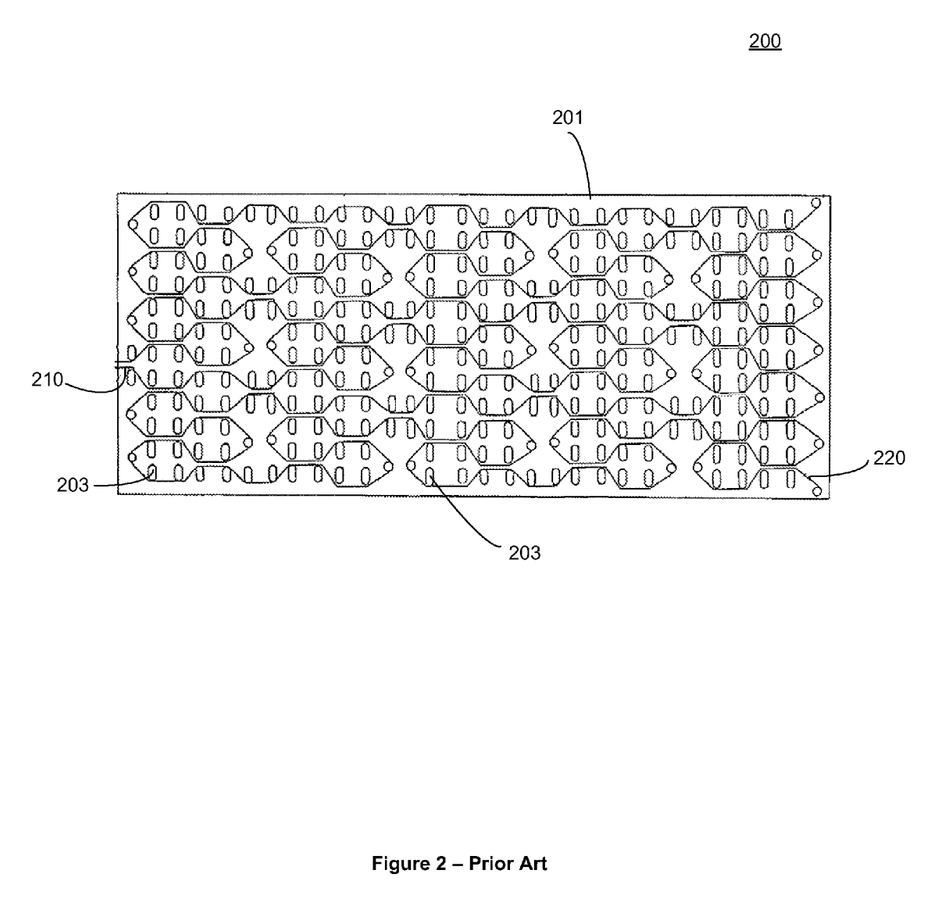
FIG. 2 illustrates a flat projection representing a planar view of a mandrel surface with pins of the prior art.

Stents such as stent 102 of FIG. 1 can be formed by using known stent forming devices similar to the stent-forming device 200 illustrated in FIG. 2. Stent-forming device 200 comprises a frame 201. In such configurations, frame 201 can comprise a cylindrical frame that is generally similar to the final shape of stent 102, upon the surface of which a plurality of pins 203 is placed. Pins 203 are typically placed in an arrangement that corresponds with the desired pattern for stent 102. For example, pins 203 can be arranged in a pattern 220.

With such devices, a wire 210 is manually wound through pins 203 across frame 201. As wire 210 is wound through pins 203, the wire bends to conform to the pattern 220 of pins 203. Once wire 210 has been wound through pins 203, stent 102 is formed. Stent 102 is then removed from the stent-forming device 200. Because wire 210 must be wound through pins 203, such stent-forming devices can be time and labor intensive.

In various embodiments of the present disclosure, an improved stent formation device 300 that reduces time and labor is provided. For example, in an embodiment such as that illustrated in FIG. 3A, improved stent formation device 300 comprises a mandrel 306 having an outer surface 308 with one or more grooves 312 configured in a pattern 320. A wire guide, such as, for example, a collar 314 is configured to slide and rotate about outer surface 308 of mandrel 306. A wire 110 is provided to mandrel 306 and collar 314, and collar 314 can be manipulated to force wire 110 to conform to groove 312, forming stent 102. Stent 102 can be further used to form a stent-graft or other endoluminal devices.

Figure 3A:
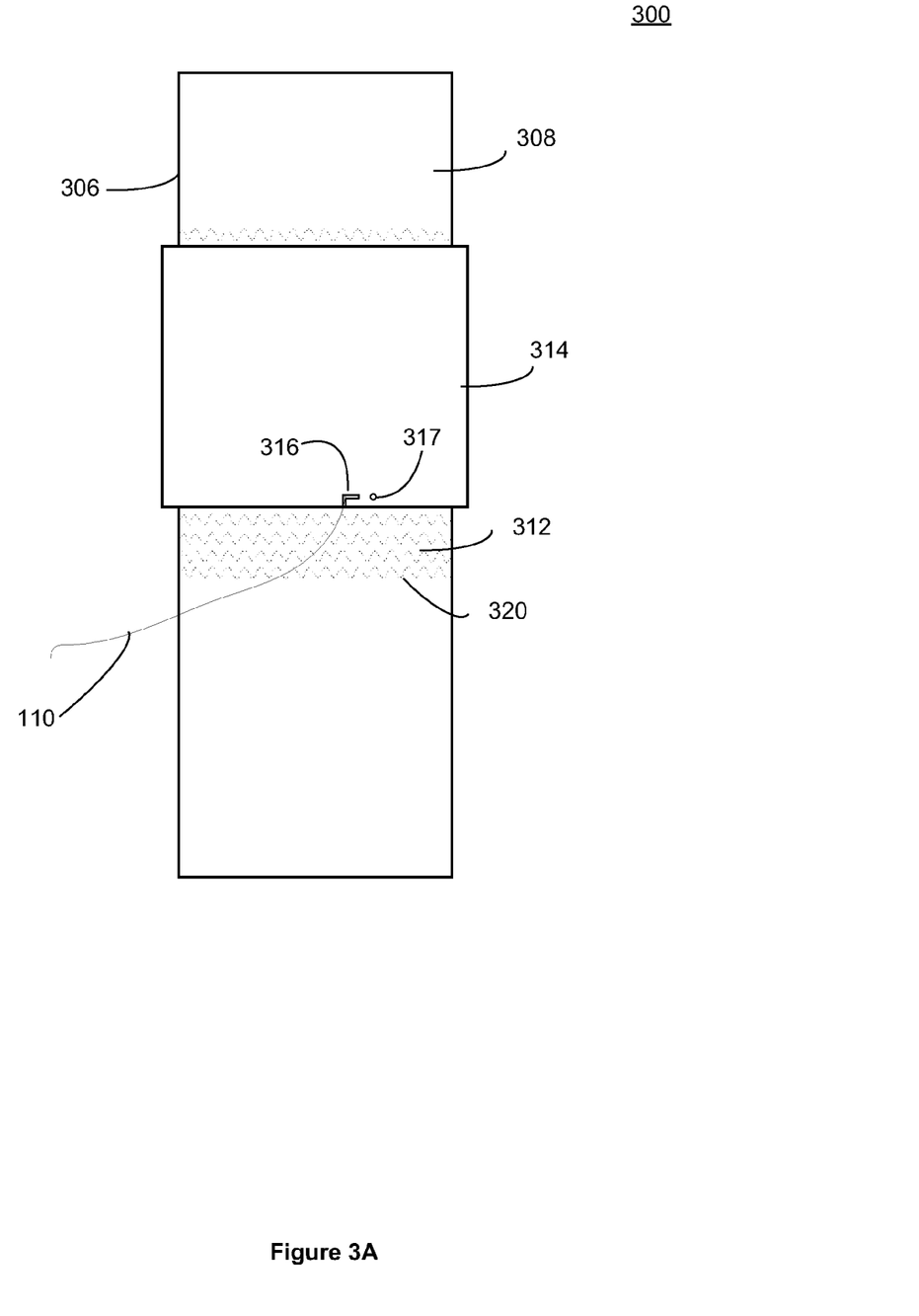
FIGS. 3A-3D illustrate a side view, a close up view, a side view, and a top view, respectively, of stent formation devices in accordance with the present disclosure.

As illustrated in FIG. 3A, in an embodiment, mandrel 306 can be a cylindrical shaft around which a stent, such as stent 102, is formed. The diameter of mandrel 306 can generally correspond with the desired diameter of stent 102. Further, the length of mandrel 306 and/or pattern 320 can generally correspond with the desired length of stent 102.

Mandrel 306 can comprise, for example, a metal cylinder, whether hollow or solid. In such embodiments, mandrel 306 can comprise steel, aluminum, titanium, or the like.

In other embodiments, mandrel 306 can comprise a non-metallic cylinder, again, whether hollow or solid. In such embodiments, mandrel 306 can comprise polyvinyl chloride (PVC), polystyrene, acrylonitrile butadiene styrene (ABS), among other polymers. In general, any material that provides sufficient structural support, rigidity and/or strength for mandrel 306, whether metallic, non-metallic, polymeric or non-polymeric, is within the scope of the present disclosure.

As noted above, in various embodiments, mandrel 306 comprises an outer surface 308 having one or more grooves 312. In this regard, while the singular form groove 312 is generally used herein, it should be understood that in various embodiments there can be more than one groove present.

Figure 3B:
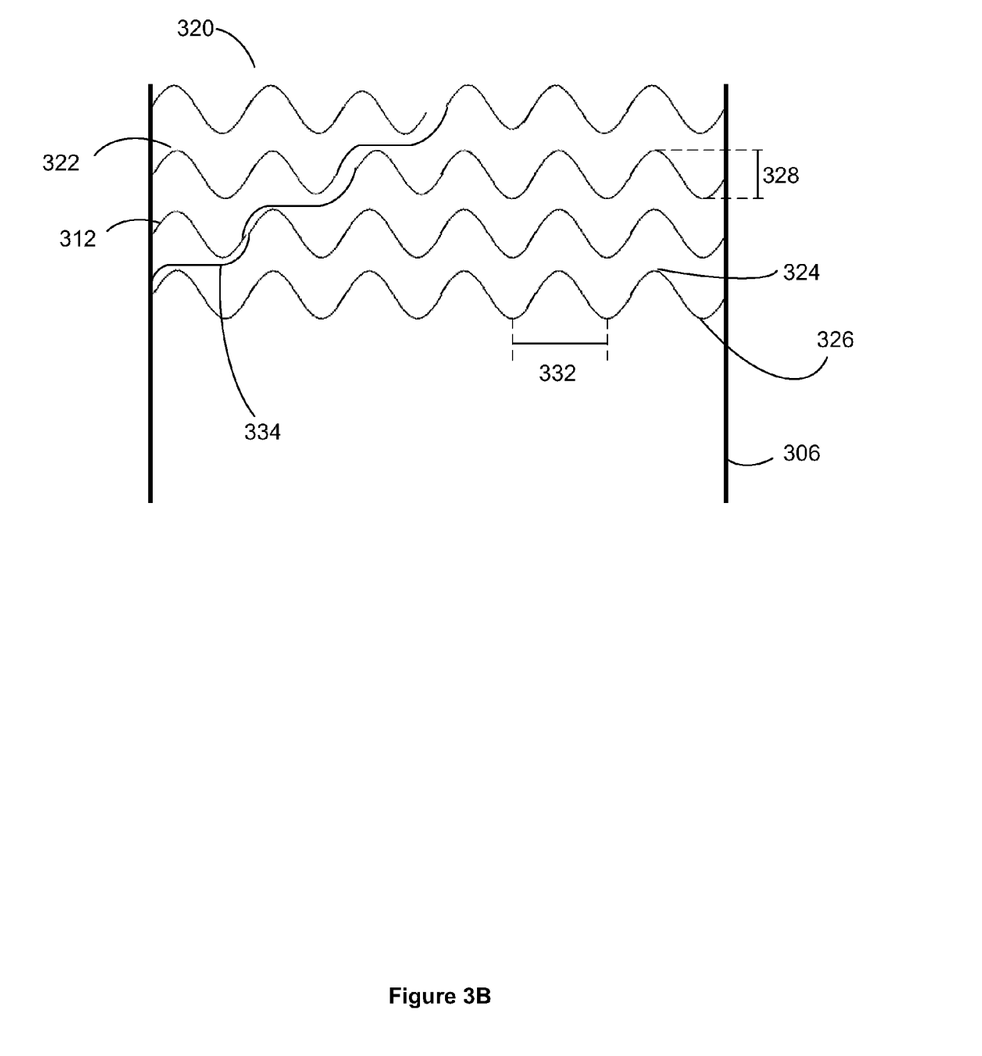

In some embodiments, groove 312 can be configured to receive wire 110 and cause it to take the same general shape as groove 312. Groove 312 can be, for example, a depression or channel in the same general profile as the cross-sectional profile of wire 110. Groove 312 can comprise a shape that assists in orienting wire 110 properly within groove 312. For example, wire 110 and groove 312 can share a cross-sectional profile having at least one axis of asymmetry, such as a teardrop shape or v-shaped notch. In such configurations, the pointed or notched section of wire 110 can be guided into the matching portion of groove 312. In various embodiments, with reference to FIG. 3B, mandrel 306 comprises groove 312 in the shape of pattern 320. Pattern 320 corresponds to the general shape of the desired stent pattern. For example, pattern 320 can comprise a single groove 312, such that stent 102 is formed from a single wire. In the embodiment of FIG. 3B, though when viewed from the side or front angles, pattern 320 appears to comprise a plurality of individual rows 322, pattern 320 is actually a single continuous groove 312. Further, rows 322 can be substantially concentric and perpendicular to a longitudinal axis of collar 314 and/or a longitudinal axis of mandrel 306.

For example, in such configurations, pattern 320 comprises at least one row connector 334 that connects each row 322 to the row or rows 322 adjacent to it. Thus, in some embodiments, a single wire 110 can be continuously fed into improved stent formation device 300 to form a single stent 102. In various embodiments, any configuration of row connectors 334, including a combination of different types, which effectively couples adjacent rows 322 of stent 102 is within the scope of the present disclosure.

In various embodiments, rows 322 comprise a generally sinusoidal shape having peaks 324 and valleys 326. Rows 322 can further comprise a period 332 between a peak 324 and an adjacent peak 324, as well as amplitude 328 between a peak 324 and an adjacent valley 326. For example, period 332 and amplitude 328 can be constant across rows 322, such that pattern 320 comprises a consistent sinusoidal shape. In such configurations, as illustrated in FIG. 3B, pattern 320 can comprise a generally constant height and/or a generally constant length.

In various embodiments, period 332 and/or amplitude 328 can vary across row 322 and/or between adjacent rows 322. In such configurations, pattern 320 can be varied to correspond to a desired stent shape in which peaks 324 and valleys 326 vary across each row 322 and/or between adjacent rows 322. However, any pattern 320, including a sinusoidal pattern, which is capable of creating a suitably shaped stent is within the scope of the present disclosure.

With reference back to FIG. 3A, stent formation device 300 includes a collar 314. In various embodiments, collar 314 surrounds mandrel 306. Collar 314, for example, can comprise a cylindrical sleeve that concentrically surrounds mandrel 306. In such configurations, collar 314 can comprise a cylinder of lesser height than the height of mandrel 306.

In various embodiments, and as described in more detail below, collar 314 is configured to slide and rotate relative to outer surface 308 of mandrel 306. In such configurations, sliding and rotating collar 314 exerts pressure on wire 110. This pressure causes wire 110 to conform to groove 312 and take the general shape of pattern 320. In a number of embodiments, the collar 314 can have sufficient axial length to cover the groove 312 and maintain the wire 110 in the groove 312, as the collar 314 is displaced axially along and rotated relative to the mandrel 306. For example, the collar 314 can be provided with sufficient length to cover all of the grooves or length of the resulting formed stent.

In various embodiments, collar 314 can comprise, for example, a metal sleeve. In such embodiments, collar 314 can comprise steel, aluminum, titanium, or the like.

In other embodiments, collar 314 can comprise a non-metallic sleeve. In such embodiments, collar 314 can comprise polyvinyl chloride (PVC), polystyrene, acrylonitrile butadiene styrene (ABS), among other polymers. In general, any material that provides sufficient structural support, rigidity and/or strength for collar 314, whether metallic, non-metallic, polymeric or non-polymeric, is within the scope of the present disclosure.

In various embodiments, collar 314 can further comprise a slot 316. In various embodiments, slot 316 of collar 314 is configured to receive and orient wire 110. Wire 110 is fed through slot 316 to a position between collar 314 and at least one groove 312 of outer surface 308.

Figure 6A:
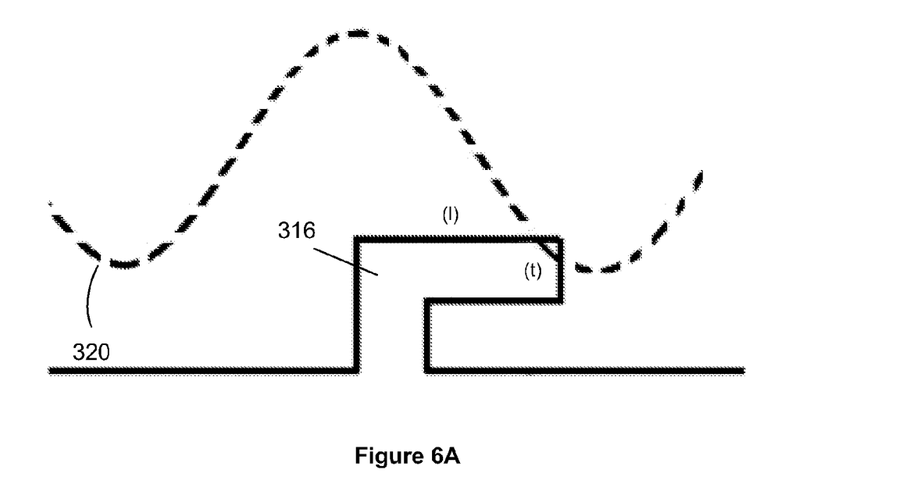
FIGS. 6A-6D illustrate close up views of a stent formation device in accordance with the present disclosure in various stages of operation.

In various embodiments and with momentary reference to FIG. 6A, slot 316 can comprise an aperture in collar 314 having a length (l) and a thickness (t) greater than the diameter or thickness of the wire. For example, slot 316 can be oriented generally perpendicularly to a longitudinal axis of collar 314 and/or a longitudinal axis of mandrel 306. The length (l) of slot 316 can correspond with a desired attribute of the stent. For example, the length of slot 316 can be generally half of the distance between the peaks 324 and/or valleys 326 of stent 102. The length of the slot 316 can, in a number of embodiments, be longer than the distance between the peaks 324 and/or valleys 326 of the stent 102. Further, the thickness of slot 316 can be greater than the width of wire 110 and/or groove 312.

In various embodiments, slot 316 can comprise an "L"-shaped aperture. Further, the dimensions of the aperture of slot 316 can be chosen to improve visibility of pattern 320 and/or groove 312. In other embodiments, slot 316 can comprise a circular or oval-shaped aperture. For example, slot 316 can comprise a substantially cylindrical hole of a slightly larger diameter than wire 110. Any configuration of slot 316 that can receive wire 110 and position it between groove 312 of outer surface 308 and collar 314 is within the scope of the present disclosure.

Collar 314 can further comprise a viewing window 317. In various embodiments, viewing window 317 comprises a hole in collar 314 that allows an operator to view a portion of pattern 320. For example, viewing window 317 can be configured to allow an operator to view a point on pattern 320 located one or more periods 332 and/or amplitudes 328 from the position of slot 316. In such configurations, viewing window 317 can assist operator in determining the position of collar 314 relative to pattern 320 and/or groove 312.

In various embodiments, slot 316 can include a tapered portion. The tapered portion can assist in feeding wire 110 between collar 314 and at least one groove 312 of outer surface 308. The tapered portion can also assist in viewing the position of collar 314 and slot 316 relative to outer surface 308 and pattern 320.

Figure 4A:
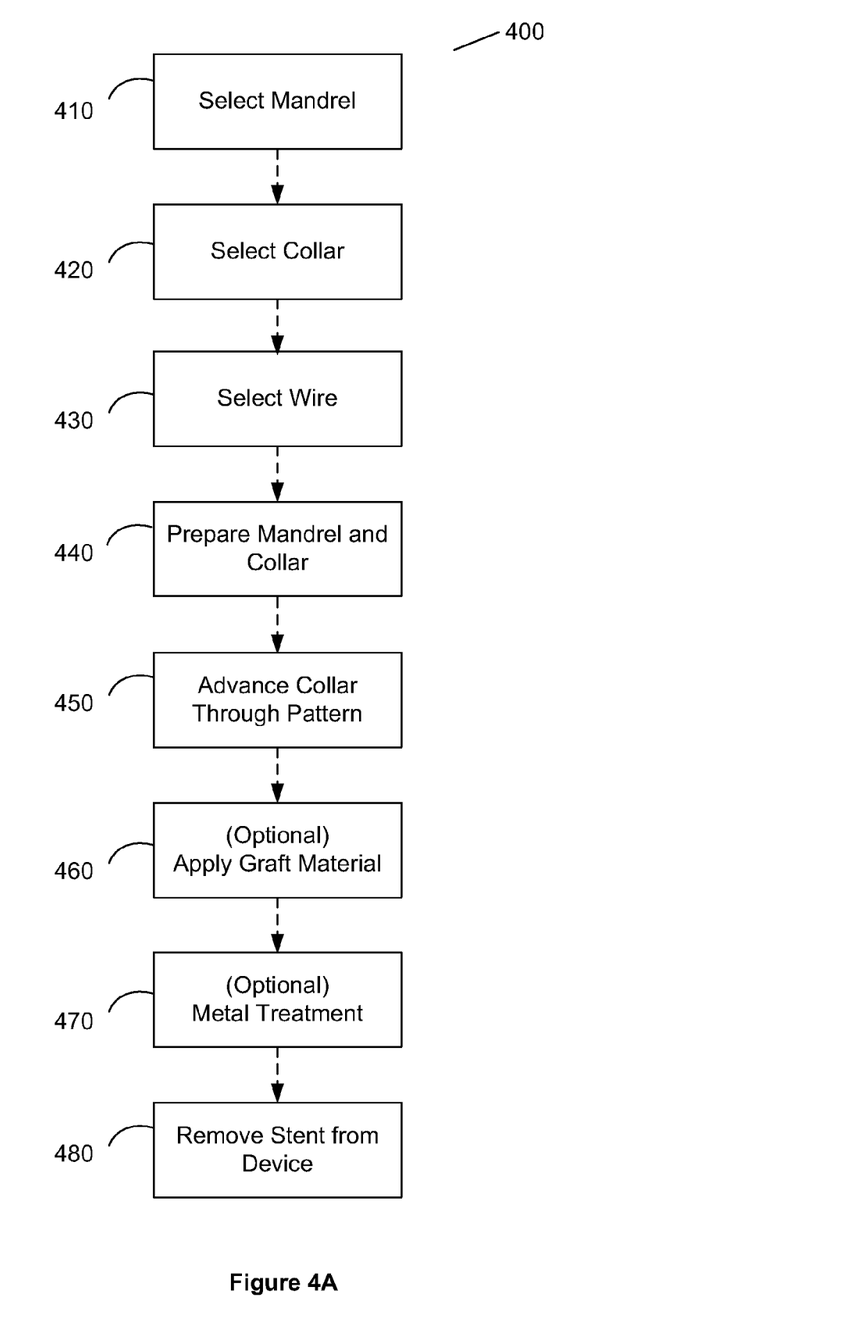
FIGS. 4A and 4B illustrate flow charts of stent formation methods in accordance with the present disclosure.

With reference to FIG. 4A, a stent formation method 400 in accordance with the present disclosure is illustrated. Stent formation method 400 uses a device, such as stent formation device 300, to create a stent, such as stent 102. Method 400 can begin with a select mandrel step 410. Select mandrel step 410 can comprise, for example, choosing a mandrel 306 with a diameter and a length that generally corresponds to the desired diameter and length of stent 102.

Further, select mandrel step 410 can comprise choosing a mandrel 306 with at least one groove 312 having a pattern 320 that corresponds to desired characteristics of stent 102. Stated another way, a mandrel is chosen with a pattern 320 that approximates the desired pattern of stent 102.

Once an appropriate mandrel 306 is selected, method 400 can further comprise a select collar step 420. Select collar step 420 can comprise choosing a collar 314 that corresponds to mandrel 306 chosen in select mandrel step 410. For example, collar 314 can have a slightly larger inner diameter than the outer diameter of mandrel 306. In various embodiments, collar 314 is chosen such that it can slide and rotate in relation to mandrel 306.

Stent formation method 400 can further comprise a select wire step 430. In various embodiments, select wire step 430 can comprise choosing a wire 110 to form stent 102 having desired qualities. For example, wire 110 can be of a desired material and selected to have a desired cross-sectional profile, thickness, flexibility, and resilience, among others. Wire 110 can be selected to attain any suitable qualities of stent 102.

After a suitable wire 110 is selected, stent formation 400 can comprise a prepare device step 440. In various embodiments, prepare device step 440 comprises positioning collar 314 around mandrel 306 in preparation for forming stent 102. Prepare device step 440 can further comprise providing wire 110 to slot 316 after collar 314 is in position relative to mandrel 306.

In various embodiments, stent formation method 400 further comprises an advance collar through pattern step 450. Advance collar through pattern step 450 can comprise, for example, moving and rotating collar 314 relative to outer surface 308 of mandrel 306. Such moving and rotating is done in a pattern which causes wire 110 to conform to groove 312, producing stent 102 having shape and size that corresponds to pattern 320.

Figure 5A:
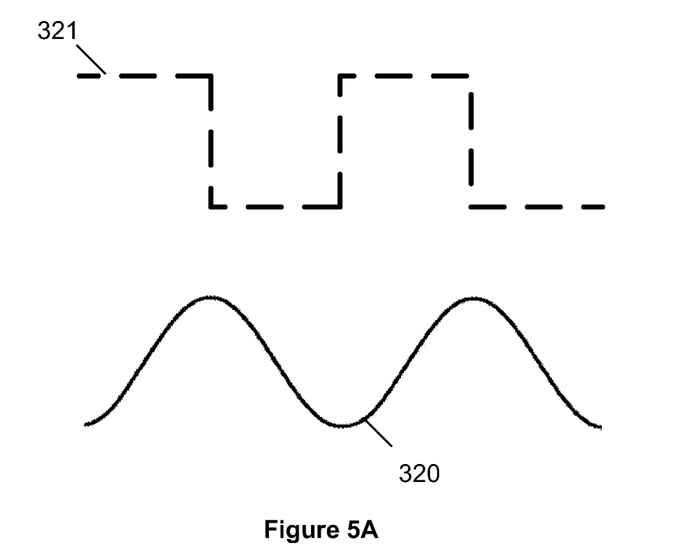
FIGS. 5A-5D illustrate close up views of stent formation devices and the motion used with the devices in accordance with the present disclosure.
Figure 5B:
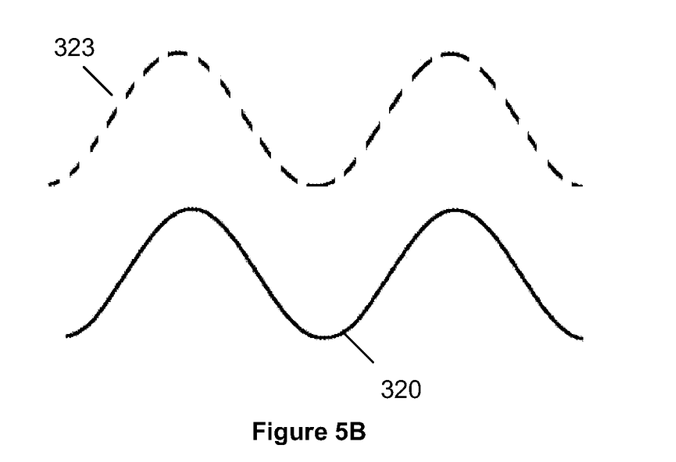

With reference to FIGS. 5A and 5B, advance collar through pattern step 450 can comprise conforming wire 110 to pattern 320 by manipulating collar 314 according to a displacement profile, such as displacement profiles 321 and 323. Displacement profiles 321 and 323 illustrate, in phantom, simplified, two-dimensional representations of the path traveled by collar 314 during advance collar through pattern step 450.

For example, as illustrated in FIG. 5A, advance collar through pattern step 450 can comprise manipulating a collar 314 with an L-shaped slot 316 according to displacement profile 321. In various embodiments, displacement profile 321 comprises a generally square wave-shaped path.

In other embodiments, as illustrated in FIG. 5B, using a collar 314 with a generally circular slot 316, an operator can produce a stent having pattern 320 by manipulating collar 314 and slot 316 according to displacement profile 323. Displacement profile 323 can comprise, for example, a generally sine wave-shaped path.

Figure 4B:
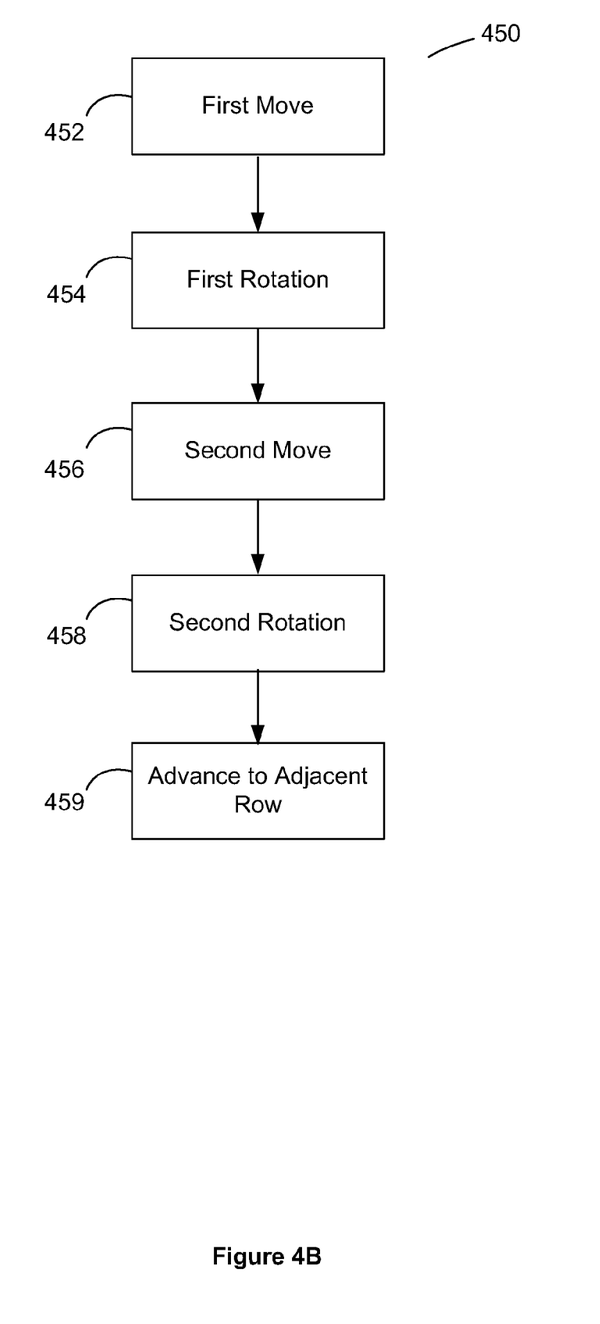

With reference to FIG. 4B, advance collar through pattern step 450 can comprise a first move step 452. In first move step 452, collar 314 can be moved longitudinally relative to outer surface 308 of mandrel 306. For example, an operator can visually identify the position of collar 314 relative to pattern 320 using slot 316. Collar 314 can then be moved a desired distance along pattern 320 through slot 316. First move step 452 can be completed once the operator has visually confirmed that collar 314 is in the desired position. The amount of displacement of first move step 452 can correspond to amplitude 328 of pattern 320. For example, collar 314 can be moved such that a point on collar 314, such as a particular edge of slot 316, travels longitudinally a distance equal to amplitude 328.

With reference to FIGS. 6A-6D, pattern 320 and slot 316 of stent formation device 300 are illustrated, for example, through the advance collar through pattern step 450 of FIG. 4A. In each of the Figures, a section of pattern 320 is not visible because collar 314 surrounds outer surface 308. The section of pattern 320 covered by collar 314 is represented in FIGS. 6A-6D by phantom lines. Thus, first move step 452 can comprise, for example, moving collar 314 from the position illustrated in 6A to the position illustrated in 6B.

Figure 6B:
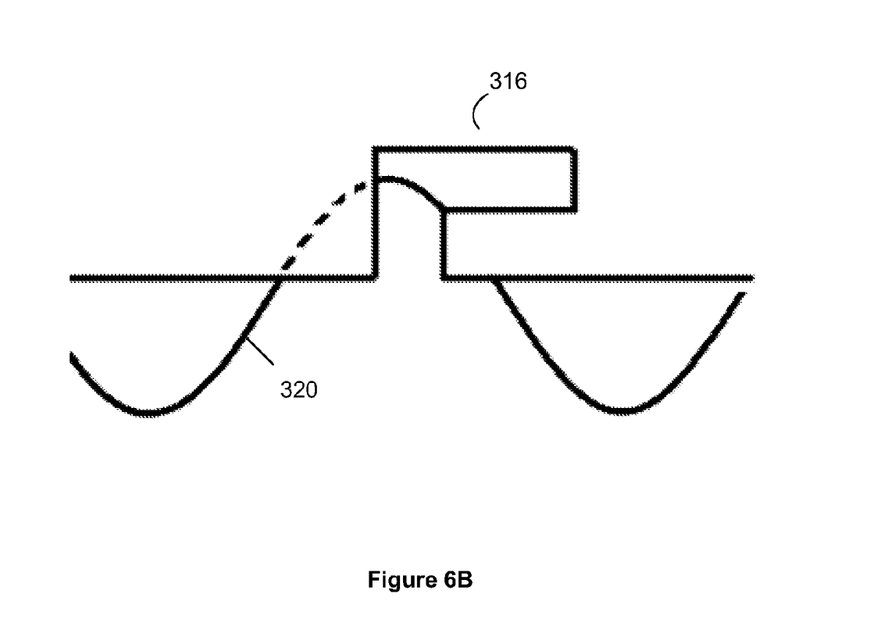
Figure 6C:
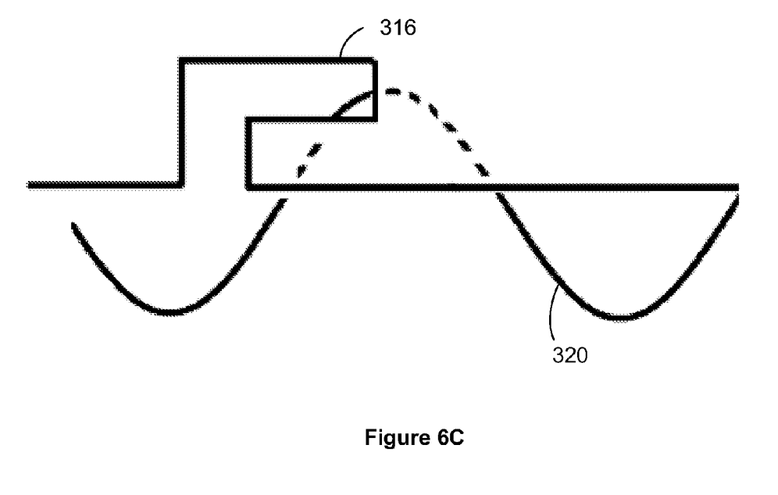

In various embodiments, advance collar through pattern step 450 can further comprise a first rotation step 454. First rotation step 454 can comprise rotating collar 314 in relation to outer surface 308 of mandrel 306. For example, an operator can visually identify the position of collar 314 relative to pattern 320 using slot 316. Collar 314 can then be rotated a desired amount along pattern 320 through 316. First rotate step 454 can be completed once the operator has visually confirmed that collar 314 is in the desired position.

The degree of rotation of first rotation step 454 can correspond to a desired distance, such as, for example, one-half of period 332 of pattern 320. Stated another way, collar 314 can be rotated such that a point on collar 314, such as an end of slot 316, travels circumferentially a distance equal to one half of period 332. First rotation step 454 can comprise, for example, rotating collar 314 from the position illustrated in 6B to the position illustrated in 6C.

Figure 6D:
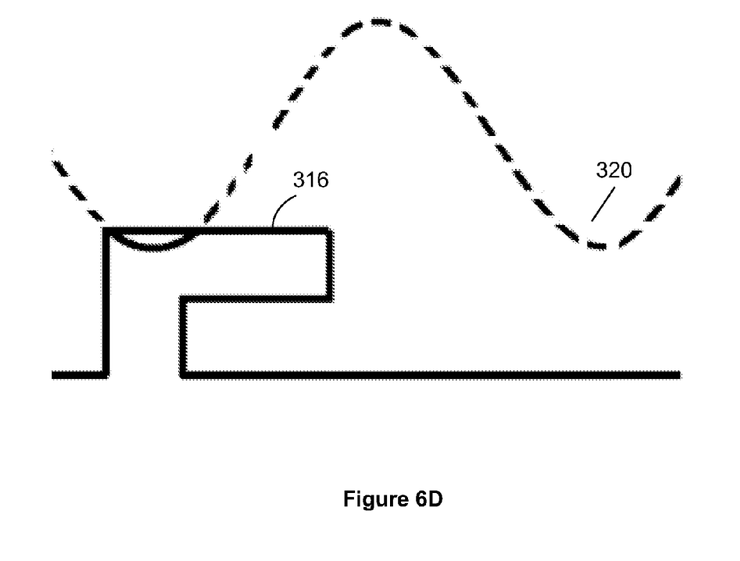

In various embodiments, advance collar through pattern step 450 further comprises a second move step 456. In second move step 456, similar to first move step 452, collar 314 can be moved longitudinally relative to outer surface 308 of mandrel 306. For example, an operator can visually identify the position of collar 314 relative to pattern 320 using slot 316. Collar 314 can then be moved a desired distance along pattern 320 through 316. Second move step 456 can be completed once the operator has visually confirmed that collar 314 is in the desired position.

In various embodiments, collar 314 can be moved the same longitudinal distance, in the opposite direction, as in first move step 452. In other embodiments, collar 314 can be moved a greater or lesser longitudinal distance as in first move step 452. For example, second move step 456 can comprise moving collar 314 from the position illustrated in 6C to the position illustrated in 6D.

Advance collar through pattern step 450 further comprises a second rotation step 458. Second rotation step 458 can comprise, similarly to first rotation step 454, rotating collar 314 relative to outer surface 308 of mandrel 306, similar to first rotation step 454. As in first rotation step 454, For example, an operator can visually identify the position of collar 314 relative to pattern 320 using slot 316. Second rotation step 458 can comprise rotating collar 314 in the same direction and for the same distance as first rotation step 454. In other embodiments, second rotation step 458 can comprise rotating collar 314 more or less than first rotation step 454. Second rotation step 458 can be completed once the operator has visually confirmed that collar 314 is in the desired position.

With reference to FIG. 6D, second rotation step 458 can comprise rotating collar 314 from the position illustrated in 6D to a position circumferentially offset by one period from the position illustrated in 6A.

Advance collar through pattern step 450 can comprise repeating steps 452, 454, 456, 458 sequentially. For example, steps 452, 454, 456, 458 are repeated until a single point of collar 314, such as, for example, slot 316, has circumferentially traversed the entire circumference of mandrel 306.

Figure 3C:
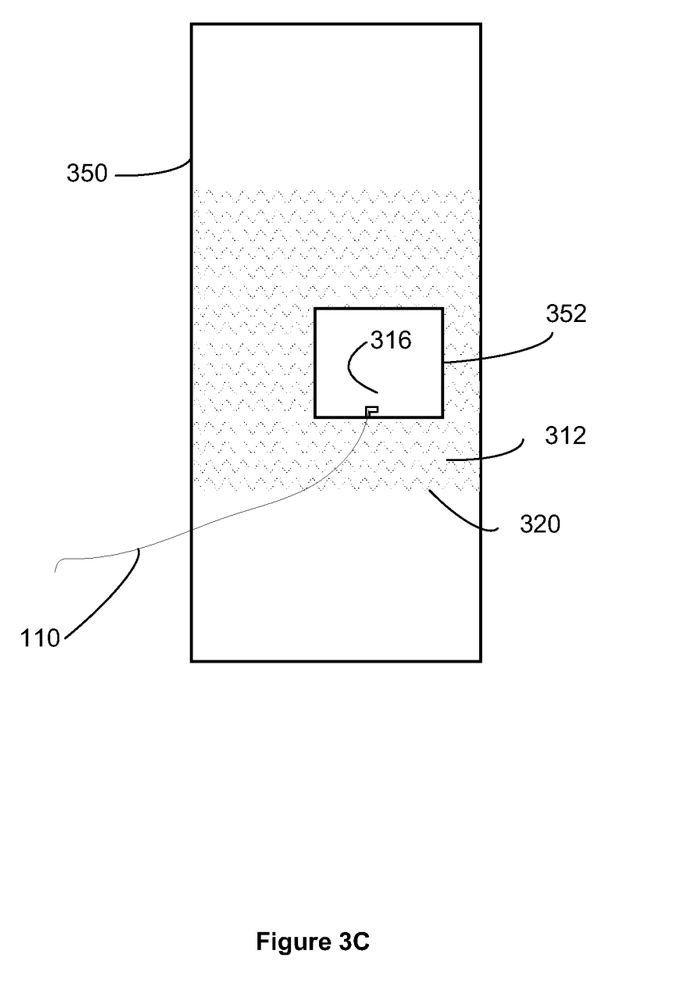
Figure 3D:
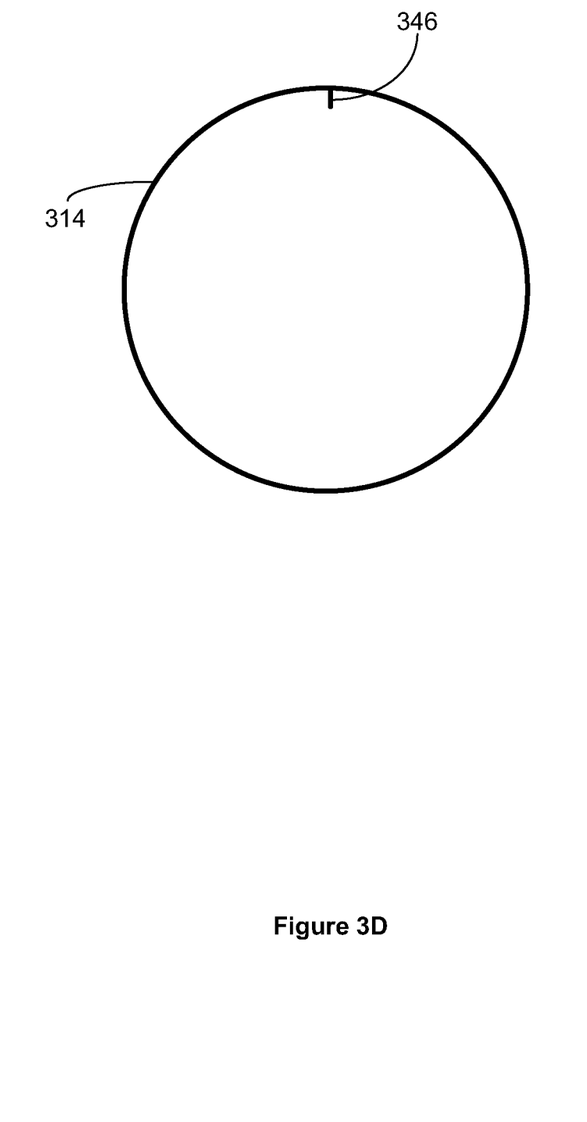

In various embodiments, with reference to FIG. 3D, collar 314 can comprise a pattern guide 346, such as a pin, configured assist an operator in performing advance collar through pattern step 450. Pattern guide 346 can be configured to assist an operator or facilitate an automated process in conforming wire 110 to a desired pattern 320 by restricting the motion of collar 314 relative to mandrel 306. For example, pattern guide 346 can engage with groove 312 to restrict the motion of collar 314 to pattern 320. In configurations where pattern 320 is substantially consistent, such as a sinusoidal wave pattern, advance collar through pattern step 450 can comprise rotating collar 314 and allowing pattern guide 346 to control the movement of collar 314 parallel to the mandrel 306 longitudinal axis.

Figure 5C:
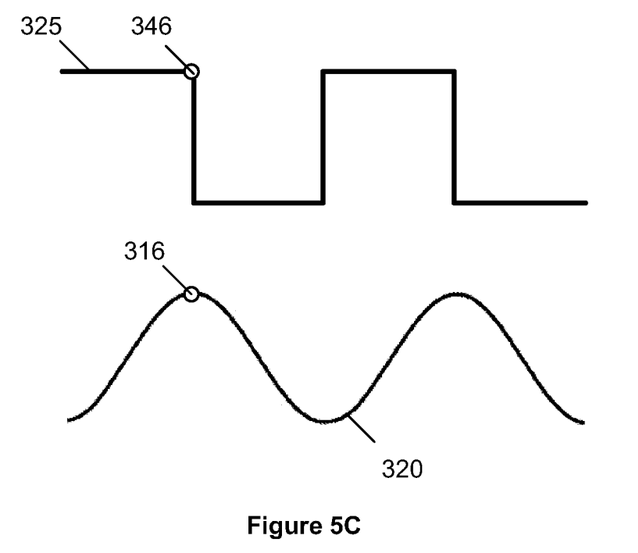

In various embodiments, pattern guide 346 can engage with a guiding groove configured to restrict the movement of collar 314 to create a desired pattern 320. For example, with reference to FIG. 5C, mandrel 308 and collar 314 having an L-shaped slot 316 are used to conform wire 110 to pattern 320. Mandrel 308 further comprises a guiding groove 325. Pattern guide 346 is positioned within guiding groove 325. In such configurations, pattern guide 346 restricts movement of collar 314 to the generally square wave path of guiding groove 325, which allows for easy automation of the stent winding process thus eliminating the need of manual operation.

Figure 5D:
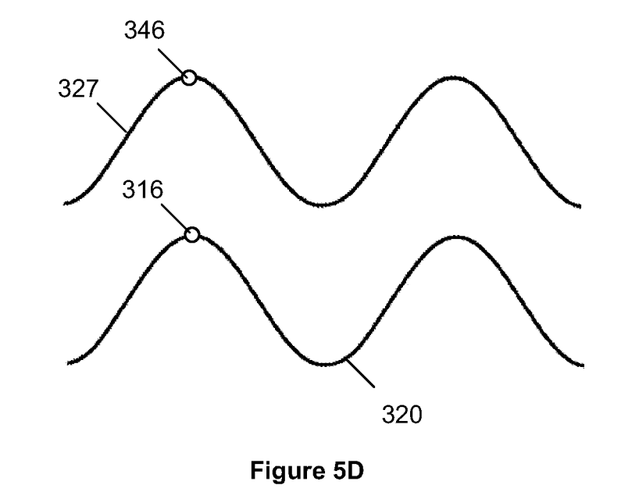

In other embodiments, mandrel 308 and collar 314 having a generally circular slot 316 are used to conform wire 110 to pattern 320. With reference to FIG. 5D, mandrel 308 can further comprise a guiding groove 327. Guiding groove 327 can comprise a generally sinusoidal path. In such configurations, pattern guide 346 engages guiding groove 327 and restricts the movement of collar 314 to the generally sinusoidal path. Any manner of utilizing a pattern guide to assist in producing a desired pattern, including one or more guiding grooves, is within the scope of the present disclosure.

In yet other embodiments, pattern guide 346 can engage groove 312 to assist in conforming wire 110 to pattern 320. For example, pattern guide 346 may be positioned one period 332 ahead of the position of slot 316 along groove 312. In configurations in which pattern 320 is substantially consistent, pattern guide 346 can be positioned a number of periods 332 ahead of the position of slot 316 on pattern 320.

In various embodiments, once steps 452, 454, 456, 458 have been sufficiently repeated, stent formation method 400 can further comprise an advance to adjacent row step 459. Advance to adjacent row step 459 can comprise, for example, rotating collar 314 relative to outer surface 308 the distance between peaks 324 and/or valleys 326. For example, after steps 452, 454, 456, 458 have been repeated sufficiently to form a row 322 of stent 102, collar 314 can be rotated such that slot 316 and wire 110 are aligned with an adjacent row 322. However, any manner of manipulating collar 314 such that wire 110 is forced to conform to row connector 334, including the use of a combination of row connectors 334, is within the scope of the present disclosure.

In other embodiments, advance collar through pattern step 450 can comprise manipulating a collar along a substantially flat surface. For example, with reference to FIG. 3C, in such embodiments, stent formation device 300 can comprise a surface 350 used with the wire guide, such as, for example, a puck 352. Puck 352 can be substantially parallel to, and positioned to be in contact with, surface 350. In such configurations, stent 102 is formed by moving puck 352 across surface 350, such that the movement of puck 352 forces wire 110 to conform to groove 312 and pattern 320 of surface 350.

In various embodiments, stent formation method 400 can further comprise an optional apply graft material step 460. The preceding steps create a stent 102, which can be further manipulated to create an endoluminal device such a stent-graft, filter, valve, anchor, occluder, or any other implantable device. For example, apply graft material step 460 can comprise creating a stent-graft from stent 102. For example, apply graft material step 460 can comprise applying a graft material, such as an ePTFE tape, to wire 110 as it is conforming to groove 312. In other embodiments, apply graft material step 460 can comprise wrapping a graft material around stent 102 after it has been formed. In yet other embodiments, apply graft material step 460 comprises applying a spray or a powder coating or a wrap to stent 102, during or after wire 110 has conformed to groove 312. The application of a graft material, such as those discussed above, at any point during the process, is within the scope of the present disclosure.

In various embodiments, a suitable graft member can comprise, for example, expanded polytetrafluoroethylene (ePTFE), polyester, polyurethane, fluoropolymers, such as perfouorelastomers and the like, polytetrafluoroethylene, silicones, urethanes, ultra high molecular weight polyethylene, aramid fibers, and combinations thereof. Other embodiments for a graft member material can include high strength polymer fibers such as ultra high molecular weight polyethylene fibers (e.g., Spectra®, Dyneema Purity®, etc.) or aramid fibers (e.g., Technora®, etc.). The graft member can include a bioactive agent. In one embodiment, an ePTFE graft includes a carbon component along a blood-contacting surface thereof. Any graft member that can be delivered by a catheter is in accordance with the present disclosure.

Stent formation method 400 can further comprise an optional metal treatment step 470. For example, optional metal treatment step 470 can comprise heat treating and/or quenching the stent formation device 300 and stent 102. Any metal treatment step 470 that improves the characteristics of stent 102 is within the scope of the present disclosure.

Once advance collar through pattern step 450 has been sufficiently repeated, stent formation method 400 can further comprise a remove stent from device step 480. For example, after stent 102, is formed, collar 314 can be removed from mandrel 306. Stent 102 can then be removed from mandrel 306 and prepared for use in the vasculature of a patient.

It will be apparent to those skilled in the art that various modifications and variations can be made in the present disclosure without departing from the spirit or scope of the disclosure. Thus, it is intended that the present disclosure cover the modifications and variations of this disclosure provided they come within the scope of the appended claims and their equivalents. Likewise, numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications can be made, especially in matters of structure, materials, elements, components, shape, size and arrangement of parts including combinations within the principles of the disclosure, to the full extent indicated by the broad, general meaning of the terms in which the appended claims are expressed. To the extent that these various modifications do not depart from the spirit and scope of the appended claims, they are intended to be encompassed therein.

What is claimed is:

1. A system for forming a stent the system comprising:
   a mandrel having an outer surface, the outer surface having at least one groove configured to receive a wire therein, wherein at least a portion of the at least one groove comprises a pattern; and
   a collar being movable relative to the outer surface of the mandrel and having a slot, wherein the collar is configured to receive the wire therethrough and facilitate placement of the wire into the at least one groove during movement of the collar relative to the outer surface of the mandrel.

2. The system of claim 1, wherein the mandrel is substantially cylindrical.

3. The system of claim 1, wherein the collar is slideable and rotatable.

4. The system of claim 1, wherein the collar concentrically surrounds the outer surface of the mandrel.

5. The system of claim 1, wherein the slot is perpendicular to at least one of a collar longitudinal axis and a mandrel longitudinal axis.

6. The system of claim 1, wherein the slot is angled relative to at least one of a collar longitudinal axis and a mandrel longitudinal axis.

7. The system of claim 1, wherein the pattern comprises at least one row having a generally sinusoidal shape having a plurality of peaks and valleys, wherein the at least one row is substantially concentric and perpendicular to a mandrel longitudinal axis.

8. The system of claim 7, further comprising a plurality of rows.

9. The system of claim 7, wherein the slot has a length equal to half of a circumferential distance between an adjacent peak and valley.

10. The system of claim 1, wherein the collar further comprises a pattern guide.

11. The system of claim 10, further comprising a guiding groove, wherein the pattern guide is a pin engaged with the guiding groove.

12. A system for forming a stent, the system comprising:
    a mandrel having an outer surface, the outer surface having at least one groove configured to receive a wire therein; and
    a collar having a longitudinal axis, the collar configured to be slidable and rotatable along the mandrel outer surface and having a slot oriented substantially perpendicularly to the longitudinal axis of the collar configured to receive the wire therethrough and facilitate placement of the wire into the at least one groove.

13. The system of 12, wherein the slot has a thickness equal at least to a width of the at least one groove.

14. The system of 12, wherein the at least one groove comprises a pattern having at least one row having a generally sinusoidal shape having a plurality of peaks and valleys, wherein the at least one row is substantially concentric and perpendicular to a mandrel longitudinal axis.

15. The system of 14, wherein the pattern defines a generally constant length between adjacent peaks and a generally constant height between adjacent peaks and valleys.

16. The system of 14, wherein the slot has a length equal to at least one half of the length between adjacent peaks of the at least one groove.

17. A method of forming a stent comprising:
    providing a wire;
    providing a mandrel having an outer surface, the outer surface having at least one groove configured to receive the wire therein;
    providing a collar having a longitudinal axis, the collar being slidable and rotatable along the mandrel outer surface and having a slot oriented essentially perpendicularly to the longitudinal axis of the collar for receiving the wire therethrough and facilitating placement of the wire into the at least one groove;
    feeding the wire though slot; and
    moving and rotating the collar relative to the mandrel to conform the wire to the at least one groove.

18. The method of claim 17, further comprising a step of heat treating the mandrel, the collar, and the wire.

19. The method of claim 18, further comprising a step of quenching the mandrel, the collar, and the wire.

20. The method of claim 17, further comprising a step of applying to at least one of the mandrel and the wire a tape or a spray or a powder coating or a wrap as the collar is slid and rotated relative to the mandrel.

* * * * *